US00PP22731P2

(12) United States Plant Patent
Fear et al.

(10) Patent No.: US PP22,731 P2
(45) Date of Patent: May 15, 2012

(54) RASPBERRY PLANT NAMED 'DRISRASPFOUR'

(50) Latin Name: ***Rubus idaeus* L.**
Varietal Denomination: DrisRaspFour

(75) Inventors: Carlos D. Fear, Kent (GB); Richard E. Harrison, Aptos, CA (US)

(73) Assignee: Driscoll Strawberry Associates, Inc, Watsonville, CA (US)

( * ) Notice: Subject to any disclaimer, the term of this patent is extended or adjusted under 35 U.S.C. 154(b) by 0 days.

(21) Appl. No.: 12/928,746

(22) Filed: Dec. 17, 2010

(51) Int. Cl.
*A01H 5/00* (2006.01)

(52) U.S. Cl. ..... Plt./204

(58) Field of Classification Search ..... Plt./204
See application file for complete search history.

*Primary Examiner* — Annette Para
(74) *Attorney, Agent, or Firm* — Jondle & Associates, P.C.

(57) ABSTRACT

A new and distinct variety of raspberry plant named 'DrisRaspFour' particularly distinguished by having high yield, good flavor, and late floricane crop, is disclosed.

2 Drawing Sheets

Genus and species: *Rubus idaeus* L.
Variety denomination: 'DrisRaspFour'.

BACKGROUND OF THE NEW PLANT

The present invention relates to a new and distinct raspberry variety designated 'DrisRaspFour' and botanically known as *Rubus idaeus* L. This new raspberry variety was discovered in Santa Cruz, Calif. in September 1999 and originated from a cross between the female parent raspberry plant 'Tola' (U.S. Plant Pat. No. 11,087) and the proprietary male parent raspberry plant 'R605.1' (unpatented). The original seedling of the new variety was asexually propagated at a nursery in Santa Cruz, Calif. 'DrisRaspFour' was subsequently asexually propagated and underwent further testing at a nursery in Santa Cruz, Calif. for eight years. The present invention has been found to be stable and reproduce true to type through successive asexual propagations.

SUMMARY OF THE INVENTION

The following are the most outstanding and distinguishing characteristics of this new variety when grown under normal horticultural practices in Santa Cruz, Calif.:

1. High yield;
2. Good flavor; and
3. Late floricane crop.

DESCRIPTION OF THE PHOTOGRAPHS

This new raspberry plant is illustrated by the accompanying photographs which show fruit of the plant as well as the primocanes. The colors shown are as true as can be reasonably obtained by conventional photographic procedures. The photographs are of plants that are eight months old.

DESCRIPTION OF THE NEW VARIETY

Figure 1:
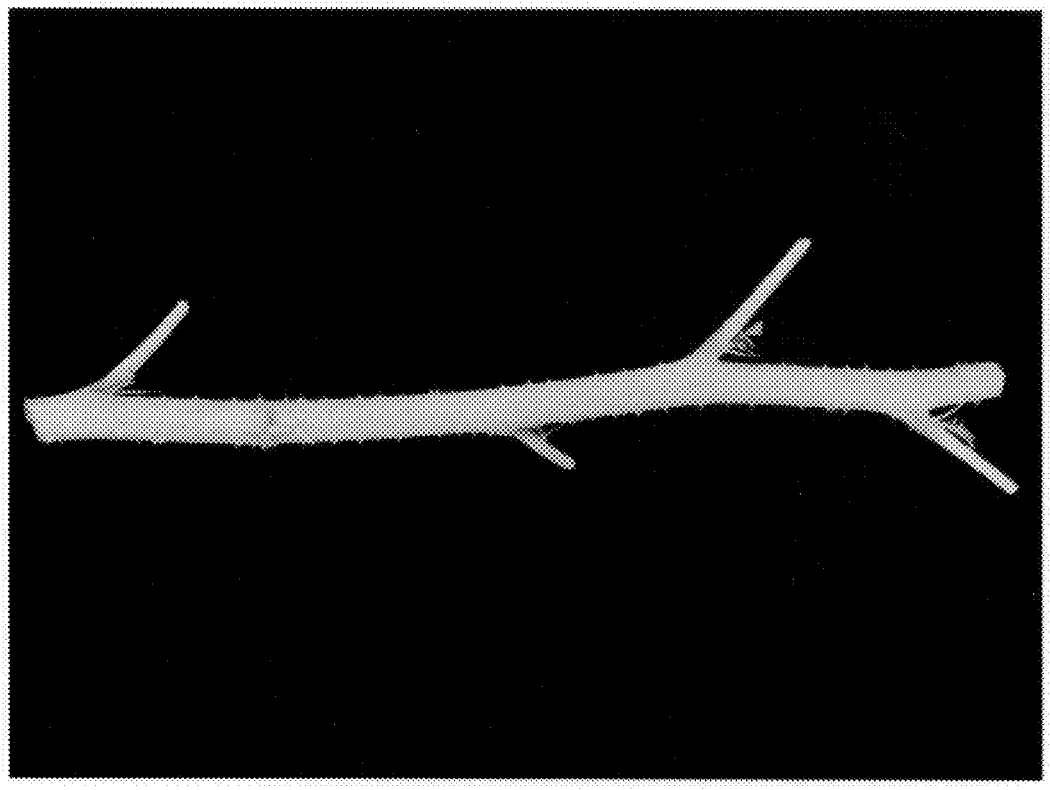
FIG. 1 shows a section of a young cane with prickles.
Figure 2:
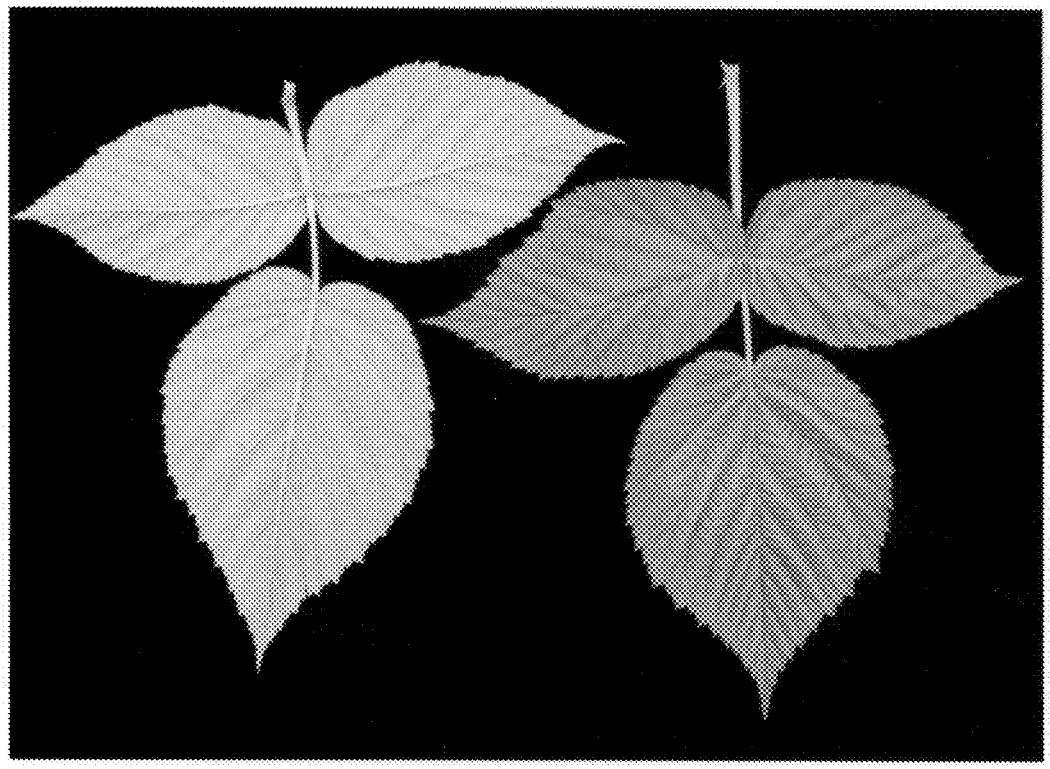
FIG. 2 shows both the upper surface and the lower surface of the plant leaves.
Figure 3:
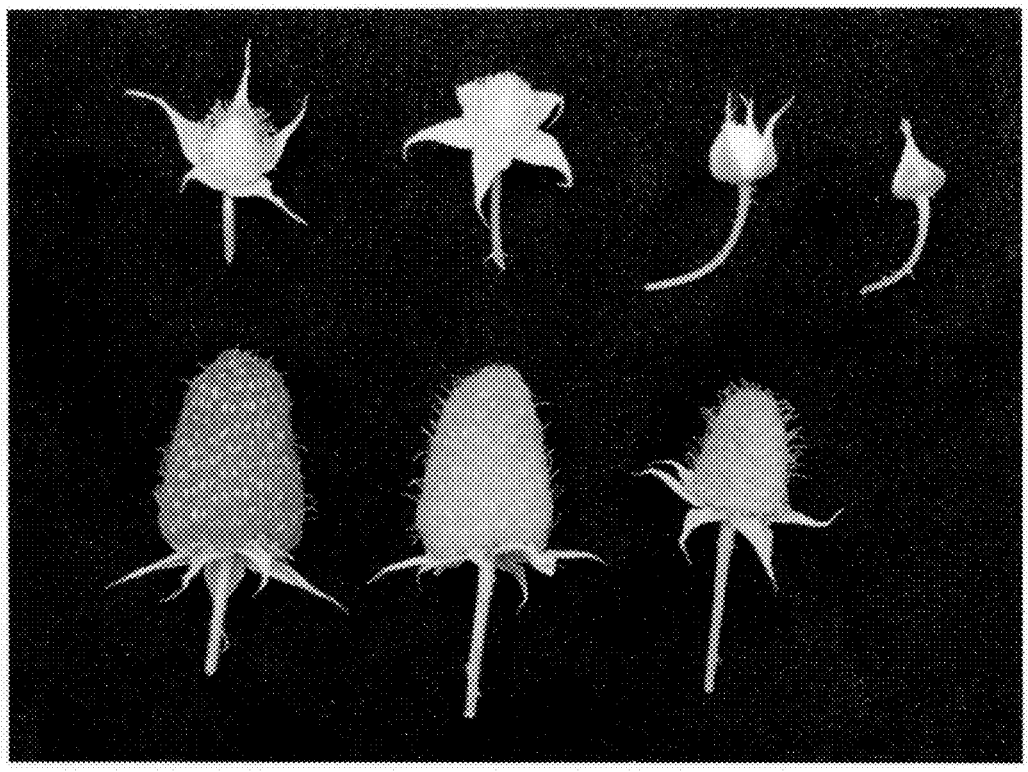
FIG. 3 shows (from left to right, from top to bottom) an immature fruit, an immature fruit, a flower bud, a flower bud, a mature fruit, an immature fruit, and an immature fruit.
Figure 4:
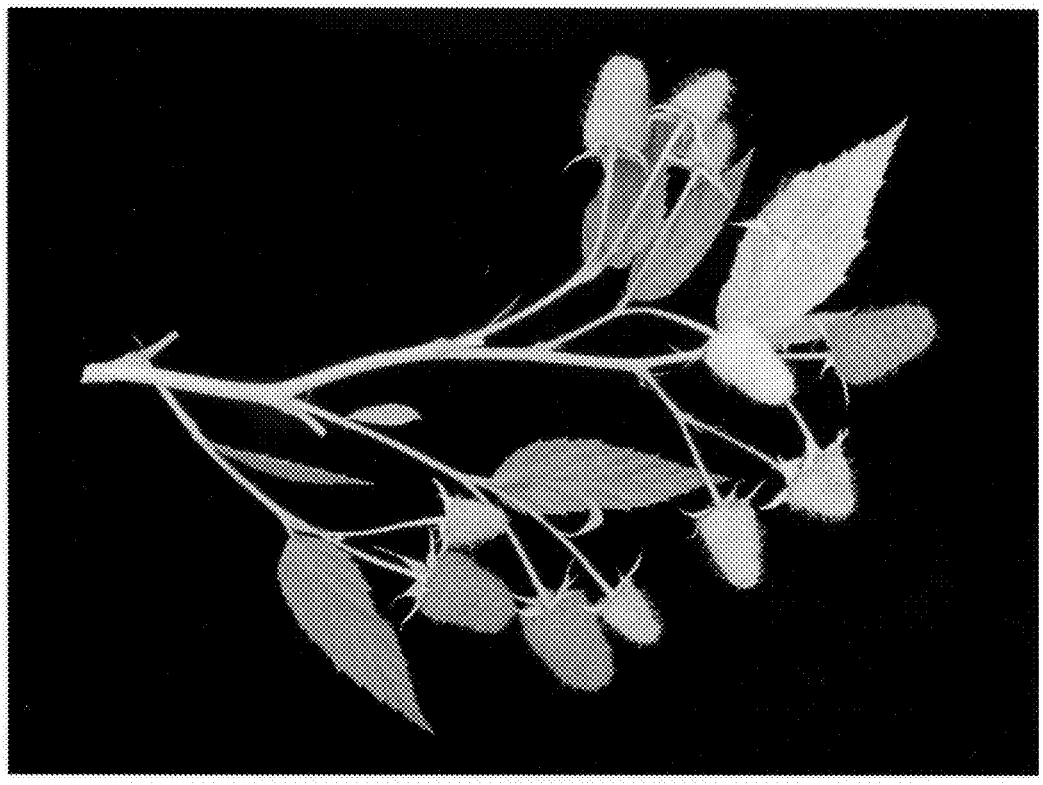
FIG. 4 shows a section of cane including fruit at various stages of development.

The following description of 'DrisRaspFour' is based on observations taken from the 2000 to 2008 growing seasons in Santa Cruz, Calif. This description is in accordance with UPOV terminology. Color designations, color descriptions, and other phenotypical descriptions may deviate from the stated values and descriptions depending upon variation in environmental, seasonal, climatic and cultural conditions. 'DrisRaspFour' has not been observed under all possible environmental conditions. Color references are primarily to the R.H.S. Colour Chart of The Royal Horticultural Society of London (R.H.S.), Fifth Edition (2007).

DETAILED BOTANICAL DESCRIPTION

Classification:
- *Family*.—Rosaceae.
- *Botanical*.—*Rubus idaeus* L.
- *Common name*.—Raspberry.
- *Variety name*.—'DrisRaspFour'.

Parentage:
- *Female parent*.—The raspberry plant 'Tola' (U.S. Plant Pat. No. 11,087).
- *Male parent*.—The proprietary raspberry plant 'R605.1' (unpatented).

Plant:
- *Propagation*.—Tissue culture and root cuttings.
- *Height*. —223.8 cm
- *Width*. —36.0 cm
- *Length/Width ratio*. —6.2
- *Size*.—Very large.
- *Productivity*.—Very high.
- *Self-fruitfulness*.—Self-fruitful.
- *New cane growth habit*.—Erect or upright.

Primocanes:
- *Number of canes*.—Many.
- *Glaucosity* (*waxy bloom*).—Medium.
- *Cane length*.—147.0 cm; Short.
- *Length of internode*.—Long.

*Length of vegetative bud*.—Medium.
*Number of young shoots*.—Medium.
*Anthocyanin coloration of apex during rapid growth*.—Present.
*Intensity of anthocyanin coloration of apex during rapid growth*.—Medium.
*Time of young shoot emergence from the soil*.—Late.
*Time of beginning of flowers*.—Medium.
*Time of beginning of fruit ripening in autumn*.—Medium.
*Length of fruiting period in autumn*.—Long.
*Percent of cane flowering as primocane*.—82%.
*Percent primocane yield of total yield*.—93%.
*Cane strength*.—Medium.
*Shape of cane cross section*.—Rounded to angular.
*Pubescence on canes*.—Absent.

Floricanes:
*Dormant cane length in summer*.—Long.
*Dormant cane color in summer*.—RHS 199D (Light greyed-brown).
*Fruiting lateral attitude*.—Erect.
*Fruiting lateral length*.—Semi-erect.
*Time of vegetative bud burst*.—Late.
*Time of beginning of flowers*.—Medium.
*Time of beginning of fruit ripening*.—Medium.
*Length of fruiting period*.—Medium.

Prickles (spines):
*Density of spines on central third*.—Dense.
*Size of base of prickles*.—Very small.
*Length* (*from base to tip*).—Between very short and short.
*Color* (*pigmentation*).—RHS 149B (Light yellow-green).
*Attitude of tip*.—Horizontal.
*Size*.—1.40 mm; Large.
*Texture*.—Soft.
*Presence and distribution on petioles*.—Present and regularly distributed.
*Internodal distance at central third of cane*.—5.10 cm.

Leaves:
*Type*.—Compound, 3 or 5 leaflets.
*Terminal leaflet*.—Length: 12.5 cm; Medium. Width: 8.5 cm; Medium. Length/Width ratio: 1.5 Leaf color: Upper surface: RHS 147A (Dark yellow green). Lower surface: RHS 147B (Medium yellow green). Profile in cross section: Flat (straight). Relief between the veins: Medium. Overlapping of leaflets: Overlapping. Glossiness: Dark. Shape: Ovate. Apex: Acuminate. Base: Obtuse. Margin: Doubly serrate. Arrangement: Compound-alternate.
*Lateral leaflets* (*basal pair*).—Number of leaflets: Sometimes 3, sometimes 5. Arrangement: Compound-alternate. Shape: Ovate. Apex: Acuminate. Base: Obtuse. Margin: Crenate. Lateral leaflet (length to stalklet, lower pair): Very short. Length: 10.2 cm. Width: 5.8 cm. Length/Width ratio: 1.8 Rachis length between the terminal leaflet and adjacent lateral leaflet: 3.10 cm.
*Petiole*.—Anthocyanin coloration: Upper surface: Absent. Lower surface: Absent. Length: 4.8 cm. Diameter: 1.6 mm Stipules:
*Orientation*.—Erect.

Flowers:
*Flower diameter (partially open (or closed))*.—8.24 mm
*Size*.—Large.
*Flowering period*.—Primocane: Medium. Floricane: Medium.
*Harvest season*.—Primocane: 9 to 16 weeks. Floricane: 5 to 8 weeks.
*Pedicel*.—Number of spines: Absent or very few. Anthocyanin coloration: Medium. Length: Medium. Length: 26.39 mm Diameter: 0.95 mm
*Petal*.—Length: 9.3 mm. Width: 4.2 mm. Length/Width ratio: 2.2

Peduncle:
*Presence of anthocyanin coloration*.—Absent.
*Intensity of anthocyanin coloration*.—Absent or very weak.

Fruit:
*Length*.—Medium, 2.56 cm.
*Width*.—Medium, 2.08 cm.
*Ratio of length to width*.—1.2, longer than broad.
*Average number of drupelets per fruit*.—97.
*Weight* (*g/fruit*).—Primocane: 4.11. Floricane: 3.75.
*Soluble solids* (*% in Brix*).—9.4.
*Titratable acidity* (*% as citric acid*).—10.9.
*Weight of seeds* (*mg/seed*).—3.36.
*Size*.—Medium.
*Shape*.—Ovate (broad conical).
*Size of single drupelet*.—Medium.
*Color*.—Immature fruit: RHS 180B (Medium greyed-red). Maturing fruit: RHS 185B (Dark greyed-purple). Mature fruit color: RHS 185A (Dark greyed-purple).
*Glossiness*.—Medium.
*Firmness*.—From medium to firm.
*Adherence to plug*.—Medium.
*Main bearing type*.—Only on current year's cane in autumn.
*Time of ripening*.—Primocane: Medium. Floricane: Medium.
*Harvest season*.—Primocane: 10 to 12 weeks. Floricane: 8 to 10 weeks.
*Yield*.—High.

Stress resistance:
*Drought*.—Moderately resistant.
*High temperatures*.—Moderately susceptible.
*Wind*.—Moderately resistant.
*High pH*.—Moderately resistant.
*High soil salt levels*.—Moderately resistant.
*Water logging*.—Susceptible.

Disease resistance:
*Botrytis fruit rot*.—Moderately resistant.
*Powdery mildew*.—Resistant.
*Leather rot*.—Resistant.
*Leaf scorch*.—Moderately resistant.
*Leaf blight*.—Moderately resistant.

COMPARISON WITH PARENTAL AND COMMERCIAL VARIETIES

'DrisRaspFour' differs from the female parent 'Tola' (U.S. Plant Pat. No. 11,087) in that 'DrisRaspFour' has larger fruit than 'Tola'. Additionally, 'DrisRaspFour' has a larger flower size than 'Tola'.

'DrisRaspFour' differs from the proprietary male parent 'R605.1' (unpatented) in that 'DrisRaspFour' is susceptible to rust, while 'R605.1' is resistant to rust.

'DrisRaspFour' differs from the commercial variety 'Driscoll Pacifica' (U.S. Plant Pat. No. 18,658) in that 'DrisRaspFour' has a later primocane production than 'Driscoll Pacifica'.

We claim:

1. A new and distinct variety of raspberry plant named 'DrisRaspFour' as described and shown herein.

* * * * *